United States Patent [19]

Jinbo

[11] Patent Number: 5,719,320
[45] Date of Patent: Feb. 17, 1998

[54] CURE-ACCELERATOR FOR EPOXY RESIN

[75] Inventor: Susumu Jinbo, Yokohama, Japan

[73] Assignee: Hodogaya Chemical Co., Ltd., Kawasaki, Japan

[21] Appl. No.: 629,223

[22] Filed: Apr. 8, 1996

[30] Foreign Application Priority Data

Apr. 28, 1995 [JP] Japan .................. 7-127361
Apr. 28, 1995 [JP] Japan .................. 7-127362

[51] Int. Cl.⁶ .............. C07C 275/00; C07C 211/00;
C07C 261/00; C01B 31/00
[52] U.S. Cl. ................ 564/51; 564/48; 564/47;
564/50; 564/64; 564/105; 564/337; 564/428;
252/182.13; 252/182.23; 252/182.29; 560/302;
560/350; 560/353
[58] Field of Search .......... 252/182.13, 182.23,
252/182.29; 564/48, 47, 64, 105, 336, 337,
428, 50, 51; 560/302, 350, 353

[56] References Cited

U.S. PATENT DOCUMENTS

| | | | |
|---|---|---|---|
| 3,956,237 | 5/1976 | Doorakian et al. | 260/47 |
| 4,273,686 | 6/1981 | Noland et al. | 260/9 |
| 4,705,842 | 11/1987 | Von Seyerl | 528/88 |
| 5,283,362 | 2/1994 | Hackl et al. | 564/48 |
| 5,414,118 | 5/1995 | Yosizato et al. | 564/51 |
| 5,576,410 | 11/1996 | Yosizato et al. | 528/64 |

*Primary Examiner*—Sharon Gibson
*Assistant Examiner*—Deanna Baxam
*Attorney, Agent, or Firm*—Oblon, Spivak, McClelland, Maier & Neustadt, P.C.

[57] ABSTRACT

A cure-accelerator for an epoxy resin, which comprises a compound of the formula (I), $$R_1R_2NCONH-Ar-NHCONR_3R_4 \qquad (I)$$

wherein $R_1$, $R_2$, $R_3$ and $R_4$ are $C_1$–$C_3$ lower alkyl groups which may be the same or different, and Ar is a substituted tolylene group of the formula (II)

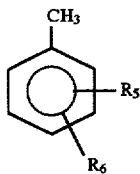

wherein $R_5$ and $R_6$ are $C_1$–$C_4$ lower alkyl groups which may be the same or different) or a 1,5-naphthylene group.

3 Claims, No Drawings

CURE-ACCELERATOR FOR EPOXY RESIN

The present invention relates to a cure-accelerator for an epoxy resin, which does not contain a halogen atom in a molecule and which is capable of curing an epoxy resin at a low temperature when it is added to a system comprising an epoxy resin and dicyandiamide. Also, the present invention relates to a novel urea derivative useful as a cure-accelerator for an epoxy resin.

An epoxy resin is excellent in various properties such as adhesive properties, mechanical strength and electric insulating properties, and is applicable to various uses having various functions when it is used in combination with a substrate resin, a curing agent, a modifier, an accelerator or the like. Thus, an epoxy resin is used in various many fields such as a paint, an adhesive, a sealing compound for electronic materials and a carbon fiber-composite material (hereinafter referred to as "CFRP"). Recently, a demand for an epoxy resin was diversified in various fields, and researches and developments have been conducted so as to satisfy the demand for various high performances.

An epoxy resin composition generally used, employs a two-pack system comprising a main pack and a curing agent pack. The main pack and the curing agent pack are stored separately, and are mixed each other at the time of using. The two-pack system composition is cured at room temperature, but has various disadvantages that a blending mistake is sometimes caused by an operator and that a pot life is limited. In order to overcome these disadvantages, a latent curing agent for one-pack type epoxy resin (a curing agent which does not react with an epoxy resin in the vicinity of room temperature but rapidly reacts with the epoxy resin when heated to a predetermined temperature) is developed. This type of a latent curing agent is dispersed in an epoxy resin, and is known to be dissolved in the presence of heat. A typical example is dicyandiamide. However, curing of this system employing this compound is slow, and it is necessary to cure this system at a high temperature. On the other hand, in order to make it applicable to various uses, the curing temperature must be made low. Also, the lowering of the curing temperature provides an advantage of saving energy. Under these circumstances, a cure-accelerator to remove the above-mentioned disadvantage of the dicyandiamide is demanded.

Examples of a cure-accelerator known at present, include a urea compound, an imidazole compound and the like, and more particular typical examples include 3-(3,4-dichlorophenyl)-1,1-dimethylura (herinafter) referred to as "DCMU"), 2-methylimidazole, and the like. However, the reactivity of an epoxy resin composition is increased in the presence of a curing agent, whereas a preservation stability (can-stability) of an epoxy resin composition is lowered, and a satisfactory composition of satisfying both the curing property and the preservation stability at the same time has not been developed up to now. Also, a compound containing a halogen atom provides a problem of corroding a metal when it is used as a sealing compound for electronic materials. Thus, there are problems to be solved in this field.

Some inventions have been made to meet the above-mentioned various demands. For example, Japanese Examined Patent Publication No. 44768/1987 discloses to improve a low temperature curability and a preservation stability by using DCMU as a cure-accelerator for a carbon fiber-reinforced epoxy resin composition without reducing heat-resistance of a cured resin. However, since DCMU contains a halogen atom in a molecule, it is hardly usable for an electronic material field and provides an environmental problem. Also, Japanese Unexamined Patent Publication No. 310890/1993 employs the above-mentioned urea compound for a composite material prepreg, but this is hardly usable for an electronic material field and provides an environmental problem on the same grounds as mentioned above.

Under these circumstances, an object of the present invention is to provide a cure-accelerator to be added to a thermoset resin composition based on an epoxy resin and dicyandiamide, which does not contain a halogen atom in a molecule and provides a satisfactory preservation stability and an excellent low temperature curability.

In order to achieve the above-mentioned object, we have studied various urea derivatives, and as the result of this study, we have discovered a novel urea derivative containing no halogen atom usable as a cure-accelerator for an epoxy resin, and also discovered that a group of urea derivatives containing no halogen atom are suitable as a cure-accelerator for an epoxy resin, which has a satisfactory preservation stability and an excellent low temperature curability.

Thus, the present invention provides a cure-accelerator for an epoxy resin, which comprises a compound of the formula (I),

wherein $R_1$, $R_2$, $R_3$ and $R_4$ are $C_1$–$C_3$ lower alkyl groups which may be the same or different, and Ar is a substituted tolylene group of the formula (II)

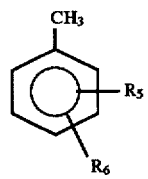

(wherein $R_5$ and $R_6$ are $C_1$–$C_4$ lower alkyl groups which may be the same or different) or a 1,5-naphthylene group.

Further, the present invention provides a method for curing an epoxy resin, characterized by using the above-mentioned urea derivative compound.

Still further, the present invention provides a novel urea derivative useful as a cure-accelerator for an epoxy resin, which has the formula (I),

wherein $R_1$, $R_2$, $R_3$ and $R_4$ methyl groups and Ar is a substituted tolylene group of the formula (II)

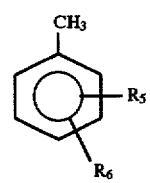

(wherein $R_5$ and $R_6$ are lower alkyl groups having a carbon number of from 1 to 4 which may be the same or different).

Particularly, a preferable cure-accelerator for an epoxy resin is a urea derivative compound of the formula (I) wherein $R_1$, $R_2$, $R_3$ and $R_4$ are methyl groups and Ar is

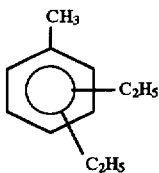

The urea derivative compound of the formula (I) wherein $R_1$, $R_2$, $R_3$ and $R_4$ are methyl groups and Ar is a substituted tolylene group of the formula (II)

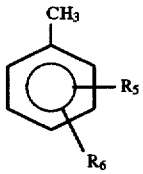

(wherein $R_5$ and $R_6$ are $C_1$–$C_4$ lower alkyl groups which may be the same or different) is a novel compound, and is expressed by the formula (I-A),

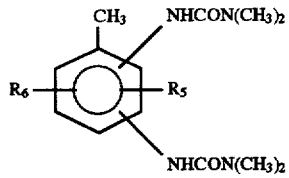

(wherein $R_5$ and $R_6$ are as defined above).

The novel urea derivative compound of the formula (I-A) of the present invention can be produced in accordance with the following methods, i.e. (i) a method which comprises reacting at least stoichiometric amount of N,N-dimethylcarbamoyl chloride with a dialkyltoluenediamine in the presence of an organic base or inorganic base and/or a phase transfer catalyst in an inert organic solvent or (ii) a method which comprises treating a dialkyltoluenediamine with phosgene to form a dialkyltoluenediisocyanate and reacting at least stoichiometric amount of dimethylamine with the dialkyltoluenediisocyanate.

In the novel urea derivatives of the formula (I-A) of the present invention, $R_5$ and $R_6$ are $C_1$–$C_4$ lower alkyl groups, examples of which include a methyl group, an ethyl group, a propyl group, an isopropyl group, a n-butyl group, an isobutyl group, a tertiary butyl group and the like, and among them, an ethyl group is most preferable.

Examples of the novel urea derivatives of the formula (I-A) of the present invention are illustrated as follows:

(a) 2,4,6-trimethyl-1,3-bis(3,3-dimethylureido)benzene,
(b) 2,5,6-trimethyl-1,3-bis(3,3-dimethylureido)benzene,
(c) 2,4,5-trimethyl-1,3-bis(3,3-dimethylureido)benzene,
(d) 2,4-diethyl-6-methyl-1,3-bis(3,3-dimethylureido)benzene,
(e) 2,5-diethyl-6-methyl-1,3-bis(3,3-dimethylureido)benzene,
(f) 4,5-diethyl-6-methyl-1,3-bis(3,3-dimethylureido)benzene,
(g) 4,5-diethyl-2-methyl-1,3-bis(3,3-dimethylureido)benzene,
(h) 2,4-dipropyl-6-methyl-1,3-bis(3,3-dimethylureido)benzene,
(i) 2,5-dipropyl-6-methyl-1,3-bis(3,3-dimethylureido)benzene,
(j) 4,5-dipropyl-6-methyl-1,3-bis(3,3-dimethylureido)benzene,
(k) 4,5-dipropyl-2-methyl-1,3-bis(3,3-dimethylureido)benzene,
(l) 2,4-diisopropyl-6-methyl-1,3-bis(3,3-dimethylureido)benzene,
(m) 4,5-diisopropyl-6-methyl-1,3-bis(3,3-dimethylureido)benzene,
(n) 2,4-dibutyl-6-methyl-1,3-bis(3,3-dimethylureido)benzene,
(o) 2,5-dibutyl-6-methyl-1,3-bis(3,3-dimethylureido)benzene,
(p) 4,5-dibutyl-6-methyl-1,3-bis(3,3-dimethylureido)benzene,
(q) 4,5-dibutyl-2-methyl-1,3-bis(3,3-dimethylureido)benzene,
(r) 2,5-di-tert-butyl-6-methyl-1,3-bis(3,3-dimethylureido)benzene,
(s) 4,5-di-tert-butyl-6-methyl-1,3-bis(3,3-dimethylureido)benzene,
(t) 4-ethyl-2,5-dimethyl-1,3-bis(3,3-dimethylureido)benzene,
(u) 5-ethyl-2,4-dimethyl-1,3-bis(3,3-dimethylureido)benzene,
(v) 2-ethyl-6-methyl-4-propyl-1,3-bis(3,3-dimethylureido)benzene, and
(w) 2-ethyl-6-methyl-5-butyl-1,3-bis(3,3-dimethylureido)benzene.

Also, in the present invention, a urea derivative compound of the formula (I) wherein Ar is a 1,5-naphthylene group, is expressed by the formula (I-B),

(wherein $R_1$, $R_2$, $R_3$ and $R_4$ are $C_1$–$C_3$ lower alkyl groups), and this compound can be produced in accordance with the following methods, i.e. (i) a method which comprises reacting at least stoichiometric amount of a di-lower alkylamine having a desired alkyl group with naphthylene-1,5-diisocyanate, or (ii) a method which comprises reacting at least stoichiometric amount of a N,N-di-lower alkylcarbamoyl chloride having a desired alkyl group with naphthylene-1,5-diamine in the presence of an organic base or inorganic base and/or a phase transfer catalyst in an inert organic solvent.

In the urea derivatives of the formula (I-B) of the present invention, $R_1$, $R_2$, $R_3$ and $R_4$ are lower alkyl groups, examples of which include a methyl group, an ethyl group, a propyl group, an isopropyl group and the like.

Examples of the urea derivatives of the formula (I-B) of the present invention are illustrated as follows:

(1) 1,5-bis(3,3-dimethylureido)naphthalene,
(2) 1,5-bis(3,3-diethylureido)naphthalene,
(3) 1,5-bis(3,3-dipropylureido)naphthalene,
(4) 1,5-bis(3,3-diisopropylureido)naphthalene,
(5) 1,5-bis(3-ethyl-3-methylureido)naphthalene,
(6) 1,5-bis(3-methyl-3-propylureido)naphthalene,
(7) 1,5-bis(3-isopropyl-3-methylureido)naphthalene,
(8) 1,5-bis(3-ethyl-3-propylureido.)naphthalene, (9) 1,5-bis(3-ethyl-3-isopropylureido)naphthalene,

(10) 1,5-bis(3-isopropyl-3-propylureido)naphthalene,

(11) 1-(3,3-dimethylureido)-5-(3,3-diethylureido) naphthalene,

(12) 1-(3,3-dimethylureido)-5-(3,3-dipropylureido) naphthalene, and

(13) 1-(3,3-dimethylureido)-5-(3-ethyl-3-methylureido) naphthalene,

The cure-accelerating effect by the urea derivative compound of the present invention is achieved with regard to a resin composition comprising a commercially available epoxy resin, dicyandiamide and the cure-accelerator of the present invention. In this case, other cure-accelerators may be additionally incorporated in the resin composition.

All of various known epoxy resins are usable as an epoxy resin used in the present invention, and the epoxy resin used in the present invention is not specially limited, but a preferable example is an epoxy resin having at least 2 epoxy groups, such as bisphenol A diglycidyl ether (Ep-808, Ep-827 and Ep-828 manufactured by Shell Chemical Co., Ltd.).

An epoxy resin composition is prepared by blending (A) an epoxy resin, (B) dicyandiamide and (C) a cure-accelerator, and the effect of the cure-accelerator of the present invention can be easily evaluated by measuring reaction heat by means of a differential scanning calorimeter (hereinafter referred to as "DSC") (Adv. Polym. Soc. 72, 112–154).

The blending amount of (B) dicyandiamide is from 2 to 15 parts by weight, preferably from 3 to 12 parts by weight, to 100 parts by weight of (A) an epoxy resin. If the blending amount of the component (B) is smaller than 2 parts by weight, curability becomes poor, and if the blending amount of the component (B) exceeds 15 parts by weight, heat resistance is lowered.

The blending amount of (C) a cure-accelerator is from 1 to 20 parts by weight, preferably from 3 to 12 parts by weight, to 100 parts by weight of (A) an epoxy resin. If the blending amount of the component (C) is less than 1 part by weight, low temperature curability becomes poor, and if the blending amount of the component (C) exceeds 20 parts by weight, heat resistance is lowered.

The epoxy resin composition of the present invention may be used in combination with the following additives depending on its use, such as a plasticizer, an organic solvent, a viscosity modifier, a fluidity modifier, a filler, a bulking agent, a pigment, a dye, a microbicide, an anti-oxidant and the like.

EXAMPLES

Now, the present invention will be described in further detail with reference to Examples. However, it should be understood that the present invention is by no means restricted to such specific Examples.

Example 1

Preparation of diethyl-methyl-1,3-bis(3,3-dimethylureido)benzene 400 ml of toluene, 50 g (0.281 mol) of diethyltoluenediamine (product of Aldemal Asano) and 68.2 g (0.674 mol) of triethylamine were charged in a 1 l four-forked flask equipped with a condenser, a thermometer and a stirrer, and 66.5 g (0.619 mol) of N,N-dimethylcarbamoyl chloride was dropwise added therein at 10°–20° C. for 1 hour. After finishing the dropwise adding, the resultant mixture was slowly heated, and was reacted at 80° C. for 3 hours. Thereafter, the reaction mixture was cooled to 10° C., and 200 ml of water was added therein under fully stirring. The resultant mixture was then filtrated, and was washed with water, and was dried to obtain 71.9 g of an aimed product (yield: 80%).

Elemental analysis values of the product were as follows:

|  | C | H | N |
|---|---|---|---|
| Theoretical value | 63.75 | 8.75 | 17.50 |
| Experimental value | 63.67 | 8.80 | 17.52 |

Result of IR(KBr) measurement: $\nu(C=O)$ 1638 cm$^{-1}$.

Example 2

10 g of an epoxy resin (Epikote-828, Yuka-Shell epoxy product), 0.7 g of dicyandiamide (Dyhard 100S SKW, Trostberg product) and 0.7 g of diethyl-methyl-1,3-bis(3,3-dimethylureido)benzene (cure-accelerator) prepared in Example 1 were fully blended and dispersed at room temperature. The reaction heat of the epoxy composition thus blended was measured by means of DSC, and it was recognized that the exothermic peak was 147° C. and that the composition was cured at this temperature. The results are shown in the following Table 1.

Example 3

The same procedure as in Example 2 was repeated, except that the amount of the cure-accelerator was changed, and the results are shown in the following Table 1.

Example 4

Preparation of 1,5-bis(3,3-dimethylureido)naphthalene 300 ml of toluene and 102.9 g (1.143 mol) of 50 wt % of dimethylamine aqueous solution were charged in a 1 l four-forked flask equipped with a condenser, a thermometer and a stirrer, and a solution having 100 g (0.476 mol) of naphthalene-1,5-diisocyanate completely dissolved in 500 ml of toluene was dropwise added therein under stirring at 15°–20° C. for 30 minutes. After finishing the dropwise addition, the resultant mixture was slowly heated, and was reacted at 50° C. for 5 hours to precipitate a crystal. The crystal thus precipitated was filtrated, washed with water and dried to obtain 139 g of an aimed product (yield: 97%).

Elemental analysis values were as follows:

|  | C | H | N |
|---|---|---|---|
| Theoretical value | 64.00 | 6.67 | 18.67 |
| Experimental value | 64.03 | 6.65 | 18.70 |

As the result of IR(KBr) measurement, $\nu(C=O)$ was 1642 cm$^{-1}$, and —NCO absorption of 2280 cm$^{-1}$ was not recognized.

Example 5

Preparation of 1,5-bis(3,3-diethylureido)naphthalene 300 ml of toluene and 83.6 g (1.143 mol) of diethylamine were charged in the same type of flask as used in Example 4, and a solution having 100 g (0.476 mol) of naphthalene-1,5-diisocyanate completely dissolved in 500 ml of toluene was dropwise added therein under stirring at 15°–20° C. for 30 minutes. After finishing the dropwise addition, the resultant mixture was slowly heated, and was reacted at 50° C. for 5 hours to precipitate a crystal. The crystal thus precipitated was filtrated, washed with water and dried to obtain 153.0 g of an aimed product (yield: 98%) having a melting point (DSC) of 223° C.

Elemental analysis values were as follows:

|  | C | H | N |
|---|---|---|---|
| Theoretical value | 65.85 | 7.32 | 17.07 |
| Experimental value | 65.80 | 7.33 | 17.05 |

As the result of IR(KBr) measurement, $\upsilon(C=O)$ was 1622 cm$^{-1}$, and —NCO absorption of 2280 cm$^{-1}$ was not recognized.

Example 6

10 g of an epoxy resin (Epikote-828, Yuka-Shell epoxy product), 0.7 g of dicyandiamide (Dyhard 100S SKW, Trostberg product) and 0.7 g of 1,5-bis(3,3-dimethylureido) naphthalene (cure-accelerator) prepared in Example 4 were fully blended and dispersed at room temperature. The reaction heat of the epoxy composition thus blended was measured by means of DSC, and it was recognized that the exothermic peak was 149° C. and that the epoxy composition was cured at this temperature. The results are shown in the following Table 1.

Example 7

The same procedure as in Example 6 was repeated, except that the amount of the cure-accelerator was changed. The results are shown in the following Table 1.

Example 8

The same procedure as in Example 6 was repeated, except that 0.7 g of 1,5-bis(3,3-diethylureido)naphthalene prepared in Example 5 was used as a cure-accelerator in place of the cure-accelerator used in Example 6. The results are shown in the following Table 1.

Example 9

The same procedure as in Example 8 was repeated, except that the amount of the cure-accelerator was changed. The results are shown in the following Table 1.

Comparative Example 1

10 g of an epoxy resin (Epikote-828, Yuka-Shell epoxy product) and 0.7 g of dicyandiamide (Dyhard 100S SKW, Trostberg product) were fully blended and dispersed without adding a cure-accelerator. The reaction heat of the epoxy resin composition thus blended was measured by means of DSC, and it was recognized that the exothermic peak was 199° C. and that the epoxy resin composition was cured at this temperature. The results are shown in the following Table 1.

Comparative Example 2

The same procedure as in Example 6 was repeated, except that 0.7 g of DCMU (Hodogaya Chemical Co. product) was used as a cure-accelerator in place of the cure-accelerator used in Example 6. The results are shown in the following Table 1.

TABLE 1

| | Epoxy resin (Epikote-828) | Dicyan-diamide (Dyhard 100S) | Cure-accelerator | Halogen atom in cure-accelerator | Change in epoxy resin composition as a lapse of time | Curing temp. (°C.) |
|---|---|---|---|---|---|---|
| Example 2 | 10 g | 0.7 g | Urea derivative of Example 1 0.7 g | Nil | No viscosity increase after a lapse of two months at room temperature | 147 |
| Example 3 | 10 g | 0.7 g | Urea derivative of Example 1 1.0 g | Nil | No viscosity increase after a lapse of two months at room temperature | 145 |
| Example 6 | 10 g | 0.7 g | Urea derivative of Example 4 0.7 g | Nil | No viscosity increase after a lapse of two months at room temperature | 149 |
| Example 7 | 10 g | 0.8 g | Urea derivative of Example 4 0.8 g | Nil | No viscosity increase after a lapse of two months at room temperature | 148 |
| Example 8 | 10 g | 0.7 g | Urea derivative of Example 5 0.7 g | Nil | No viscosity increase after a lapse of two months at room temperature | 171 |
| Example 9 | 10 g | 0.8 g | Urea derivative of Example 5 1.0 g | Nil | No viscosity increase after a lapse of two months at room | 169 |

TABLE 1-continued

| | Epoxy resin (Epikote -828) | Dicyan- diamide (Dyhard 100S) | Cure- accelerator | Halogen atom in cure- accelerator | Change in epoxy resin composition as a lapse of time | Curing temp. (°C.) |
| --- | --- | --- | --- | --- | --- | --- |
| Comparative Example 1 | 10 g | 0.7 g | Nil | — | No viscosity increase after a lapse of two months at room temperature | 199 |
| Comparative Example 2 | 10 g | 0.7 g | DCMU 0.7 g | Presence | No viscosity increase after a lapse of two months at room temperature | 153 |

By using the urea derivatives of the present invention as a cure-accelerator for an epoxy resin, the epoxy resin can be cured at a low temperature and the preservation stability of the epoxy resin can be improved. Also, since the cure-accelerator of the present invention does not contain a halogen atom in a molecule, the epoxy resin containing the cure-accelerator of the present invention provides various excellent properties when it is used as a paint, an adhesive or a CFRP, particularly as a sealing compound for electronic materials.

I claim:

1. A cure-accelerator for an epoxy resin, which comprises a compound of the formula (I),

$$R_1R_2NCONH-Ar-NHCONR_3R_4 \quad (I)$$

wherein $R_1$, $R_2$, $R_3$ and $R_4$ are $C_1$–$C_3$ lower alkyl groups which may be the same or different, and Ar is a 1,5-naphthylene group.

2. The cure-accelerator according to claim 1, wherein in the formula (I), $R_1$, $R_2$, $R_3$ and $R_4$ are methyl groups.

3. The cure accelerator according to claim 1, wherein the compound of Formula I is selected from the group consisting of 1,5-bis(3,3-dimethylureido)naphthalene, 1,5-bis(3,3-diethylureido) naphthalene, 1,5-bis(3,3-dipropylureido) naphthalene, 1,5-bis(3,3-diisopropylureido)naphthalene, 1,5-bis(3-ethyl-3-methylureido)naphthalene, 1,5-bis(3-methyl-3-propylureido)naphthalene, 1,5-bis(3-isopropyl-3-methylureido)naphthalene, 1,5-bis(3-ethyl-3-propylureido) naphthalene, 1,5-bis(3-ethyl-3-isopropylureido) naphthalene, 1,5-bis(3-isopropyl-3-propylureido) naphthalene, 1-(3,3-dimethylureido)-5-(3,3-diethylureido) naphthalene, 1-(3,3-dimethylureido)-5-(3,3-dipropylureido) naphthalene and 1-(3,3-dimethylureido)-5-(3-ethyl-3-methylureido)naphthalene.

* * * * *